(12) United States Patent
Calderone et al.

(10) Patent No.: US 9,642,846 B2
(45) Date of Patent: May 9, 2017

(54) ANTIFUNGAL DRUGS

(71) Applicant: GEORGETOWN UNIVERSITY, Washington, DC (US)

(72) Inventors: Richard A. Calderone, Chevy Chase, MD (US); Nuo Sun, Bethesda, MD (US)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 14/776,398

(22) PCT Filed: Mar. 14, 2014

(86) PCT No.: PCT/US2014/028364
§ 371 (c)(1),
(2) Date: Sep. 14, 2015

(87) PCT Pub. No.: WO2014/144097
PCT Pub. Date: Sep. 18, 2014

(65) Prior Publication Data
US 2016/0038477 A1 Feb. 11, 2016

Related U.S. Application Data

(60) Provisional application No. 61/793,090, filed on Mar. 15, 2013.

(51) Int. Cl.
*A61K 31/4745* (2006.01)
*A61K 45/06* (2006.01)

(52) U.S. Cl.
CPC .......... *A61K 31/4745* (2013.01); *A61K 45/06* (2013.01)

(58) Field of Classification Search
CPC .......................... A61K 31/4745; A61K 45/06
USPC ....................................................... 514/280
See application file for complete search history.

(56) References Cited

U.S. PATENT DOCUMENTS

2008/0038196 A1   2/2008   Beavers

FOREIGN PATENT DOCUMENTS

WO    WO 97/29106    8/1997

OTHER PUBLICATIONS

Xu et al Journal of Proteome research 2009, 8, 5296-5304.*
Lei et al., "Berberine and Itraconazole are not Synergistic in Vitro against Aspergillus Funigatus Isolated from Clinical Patients", Molecules, 2011, vol. 16, pp. 9218-9233.
Quan et al., "Potent in Vitro Synergism of Fluconazole and Berberine Chloride against Clinical Isolates of Condida Albicans Resistant to Fluconazole", Antimicrobial Agents and Chemotherapy, Mar. 2006, vol. 50, No. 3, pp. 1096-1099.
International Search Report issued in corresponding PCT International Application No. PCT/US2014/028364 and the Written Opinion.

* cited by examiner

*Primary Examiner* — Yevegeny Valenrod
(74) *Attorney, Agent, or Firm* — Klarquist Sparkman, LLP

(57) ABSTRACT

The present invention relates to the administration of compounds of formula (I) for the treatment and/or prevention of fungal infections in subjects in need thereof. The methods of the invention also relates to the administration of pharmaceutical compositions comprising compounds of formula (I) for the treatment and/or prevention of fungal infections in subjects in need thereof. Subjects suffering from fungal infection and immunocompromised subjects may particularly benefit from the methods and compositions of the invention.

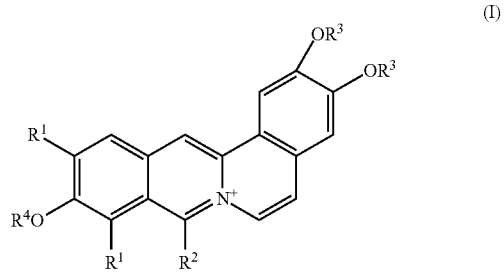

15 Claims, 2 Drawing Sheets

Drop plate assay with C. albicans

YPD

NSC156627
8µg/ml

E-test shows synergy of compound 156627 and
fluconazole against *C. albicans* wild type

YPD

NSC156627
0.4µg/ml

ANTIFUNGAL DRUGS

INCORPORATION BY REFERENCE

This application claims the benefit of priority of U.S. Provisional Application No. 61/793,090, filed Mar. 15, 2013.

The documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

Citation or identification of any document in this application is not an admission that such document is available as prior art to the present invention.

STATEMENT OF GOVERNMENT INTEREST

This invention was made in part with government support under grant number 1R21-AI090290 awarded by the U.S. National Institute of Allergy and Infectious Disease (NIAID) of the National Institutes of Health (NIH). The government has certain rights to this invention.

FIELD OF THE INVENTION

This invention relates to methods of using chemical compounds that demonstrate broad-spectrum activity against a variety of fungal infections. The chemical compounds of the invention may be administered to a subject for the treatment and/or prevention of fungal infections.

BACKGROUND

Fungal infections are major causes of morbidity and mortality. In particular, fungal infections can be life threatening for those with weakened immune systems. Severe systemic fungal infections, such as candidiasis, aspergillosis, histoplasmosis, blastomycosis and coccidioidomycosis are often acquired in hospital settings. Such infections are commonly seen in patients with suppressed immune systems.

For example, patients at risk of fungal infection include neutropaenic patients following chemotherapy and in other oncology patients with immune suppression, immune-compromised due to Acquired Immune Deficiency Syndrome (AIDS) caused by HIV infection, and in patients in intensive care. While there are treatments for candidiasis and aspergillosis, these treatments are plagued by limited efficacy, serious side effects, high expense, and often result in drug resistance.

Classes of established antifungal drugs on the market include: (1) the polyenes (e.g. amphotericin B, nystatin, natamycin), (2) the azoles (e.g. fluconazole, itraconazole, voriconazole), (3) allylamines (e.g. terbinafine), and (4) the newly introduced echinocandins (e.g. caspofungin). Of these classes, only the polyenes, azoles, and echinocandins are used to treat systemic fungal infections. Each of the currently marketed antifungal drugs have major drawbacks, including a lack of broad-spectrum activity, a lack of per oral absorption, undesirable side-effects, low antifungal activity, a lack of fungicidal activity, drug-drug interactions, and high costs. Further, the systemic antifungal, amphotericin B, is highly toxic when administered intravenously, and its side-effects include severe organ damage.

Therefore, there is a pressing need for potent antifungals for both topical and systemic infections. Treatment failures and secondary drug resistance remain common with systemic mycoses. In particular, antifungal drugs with broad spectrum activity against multiple species, per oral absorption, lower amount of side-effects, fungicidal activity, no drug-drug interactions or lower costs or a combination of these are desirable.

SUMMARY OF THE INVENTION

The present invention relates to new methods for the elimination and prophylaxis of fungal infections. The present invention provides for the treatment and prevention of fungal infections via the administration of chemical compounds and compositions described herein. In particular, the chemical compounds of the present invention exhibit broad-spectrum antifungal activity.

An embodiment of the present invention relates to the use and/or administration of a compound of formula (I):

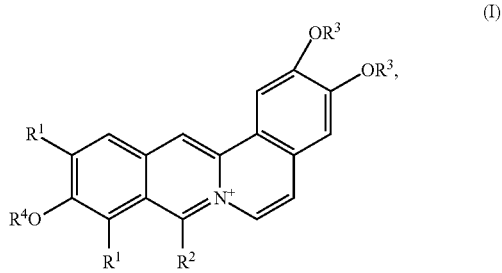

or salts thereof;
wherein
each $R^1$ is independently H or $OR^4$;
$R^2$ is H or a substituted or unsubstituted $C_1$-$C_6$ alkyl;
each $R^3$ is independently H, a substituted or unsubstituted $C_1$-$C_6$ alkyl, or the $R^3$ groups are combined as —$CH_2$— or —$CH_2$—$CH_2$— to form a 5- or 6-membered ring, respectively; and
each $R^4$ is independently H, a substituted or unsubstituted $C_1$-$C_6$ alkyl, or two adjacent $R^4$ groups are combined as —$CH_2$— or —$CH_2$—$CH_2$— to form a 5- or 6-membered ring, respectively In an embodiment, the compound of formula (I) is a compound of formula (II):

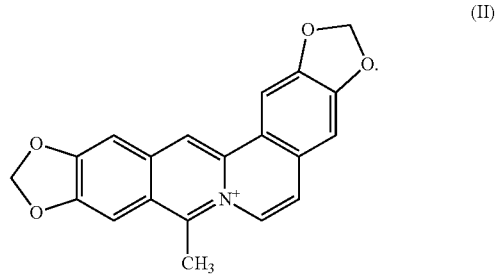 [SMILES: Cc1c2cc3c(cc2cc2c4cc5c(cc4cc[n+]12)OCO5)OCO3]

The compound of formula (II) may also be identified by its NIH-NCI identification number of 156627.

In another embodiment, the compound of formula (I) is a compound of formula (III):

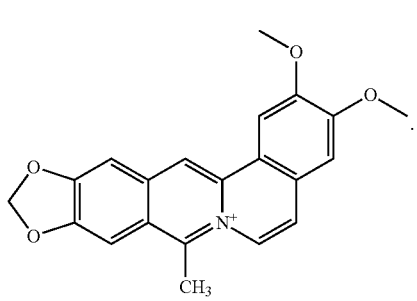

The compound of formula (III) may also be identified by its NIH-NCI identification number of 156624.

In another embodiment, the compound of formula (I) is a compound of formula (IV):

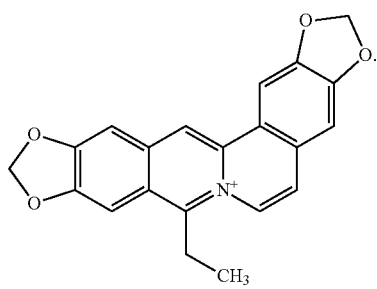

The compound of formula (IV) may also be identified by its NIH-NCI identification number of 157108.

In another embodiment, the compound of formula (I) is a compound of formula (V):

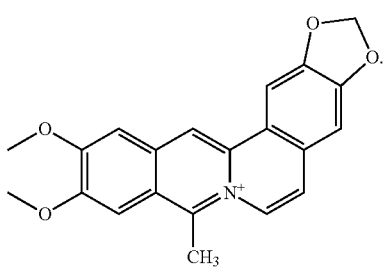

The compound of formula (V) may also be identified by its NIH-NCI identification number of 160459.

In another embodiment, the compound of formula (I) is a compound of formula (VI):

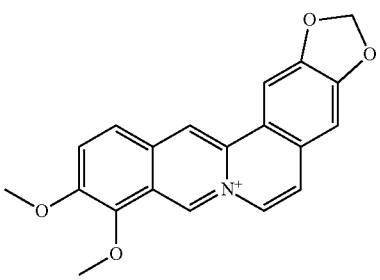 [SMILES: COc1ccc2cc3c4cc5c(cc4cc[n+]3cc2c1OC)OCO5]

The compound of formula (VI) may also be identified by its NIH-NCI identification number of 4083831.

In an embodiment, the methods of the invention comprises the administration of a compound of formula (I), (II), (III), (IV), (V), or (VI) for the treatment or prevention of fungal infections.

The compounds of formula (I) are ions, so they may be preferably present in salt form with a counter ion. Likewise, compounds of formula (II), (III), (IV), (V), (VI) may be present in salt form.

In an embodiment, the compound of formula (I) is a chloride (Cl$^-$) salt. In another embodiment, the compound of formula (I) is a salt of 2-sulfoacetate:

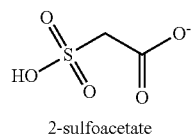

2-sulfoacetate

Methods of treating and preventing yeast or fungal infections, such as candidiasis-, aspergillosis-, and fluconazole-resistant infections, in a subject are also provided. The methods described herein, may be used against fungal infections that have developed drug resistance to one or more antifungal drugs, such as multi-drug resistant fungal strains. The methods of the invention include administering to the subject a therapeutically effective amount of the compounds and/or compositions described herein.

The methods of the present invention relate to both local and systemic administration of the compounds of the invention. Compounds and compositions of the compounds described herein may be administered to a subject in need of antifungal treatment or prevention of fungal infection. A subject in need of antifungal treatment or prevention may be a subject suffering from one or more fungal infections, or a subject that is at high risk for fungal infection. In some examples, the subject in need of antifungal treatment or preventions is immunocompromised.

The methods of treating or preventing yeast or fungal infections, as described herein, can further include administering to the subject a second compound or composition, wherein the second compound or composition includes an antifungal, an antiviral, or mixtures thereof (e.g., a triazole, a thiazole, an imidazole, a polyene, an echinocandin, an allylamine, a nucleoside polymerase inhibitor, a non-nucleoside polymerase inhibitor, a protease inhibitor, a nucleoside or nucleotide reverse transcriptase inhibitor, a non-nucleoside reverse transcriptase inhibitor, an entry inhibitor, an assembly inhibitor, and mixtures thereof).

Combination treatments combining a compound of formula (I), (II), (III), (IV), (V), or (VI) with second antifungal compound may result in a synergistic effect between the two compounds. In a specific embodiment, synergy is observed between a compound of formula (I), (II), (III), (IV), (V), or (VI) and a triazole, a thiazole, an imidazole, a polyene, an echinocandin, or an allylamine antifungal may be observed in the treatment of a fungal infection.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or encompassed by, the following Detailed Description.

DETAILED DESCRIPTION

Figure 1:
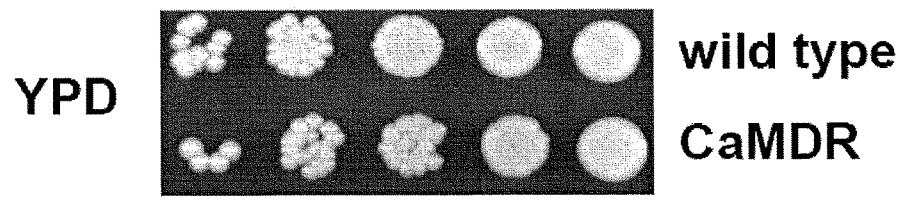
FIG. 1: A drop plate assay with *C. albicans*, wild type and multi-drug resistant (CaMDR) and NSC156627 (formula (II)).
Figure 1:
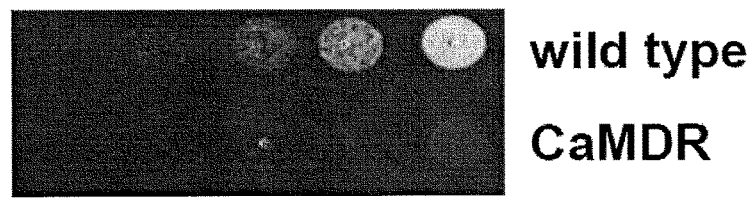

Described herein are methods of using chemical compounds that demonstrate broad spectrum activity against yeast and/or fungal pathogens. In particular, the methods the invention may be useful for the treatment or prevention of infection by fungal pathogens, such as candidiasis-, aspergillosis-, and fluconazole-resistant infections. The methods of administration described herein relate to both the systemic and local treatment of fungal infection.

In particular, the methods of the invention may be particularly valuable for the treatment and prevention of fungal infections in immunocompromised subjects, as is illustrated in more detail below.

An embodiment of the present invention relates to the use and/or administration of a compound of formula (I):

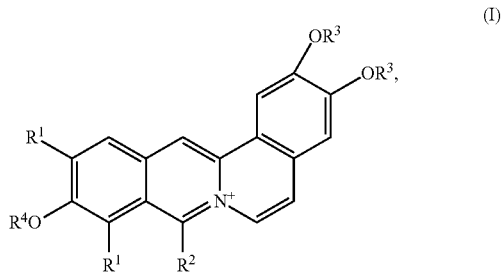

or salts thereof;
wherein
each $R^1$ is independently H or $OR^4$;
$R^2$ is H or a substituted or unsubstituted $C_1$-$C_6$ alkyl;
each $R^3$ is independently H, a substituted or unsubstituted $C_1$-$C_6$ alkyl, or the $R^3$ groups are combined as —$CH_2$— or —$CH_2$—$CH_2$— to form a 5- or 6-membered ring, respectively; and
each $R^4$ is independently H, a substituted or unsubstituted $C_1$-$C_6$ alkyl, or two adjacent $R^4$ groups are combined as —$CH_2$— or —$CH_2$—$CH_2$— to form a 5- or 6-membered ring, respectively In an embodiment of formula (I), each $R^4$ is independently a substituted or unsubstituted $C_1$-$C_6$ alkyl, or two of the $R^4$ groups are combined as —$CH_2$— or —$CH_2$—$CH_2$— to form a 5- or 6-membered ring.

In another embodiment of formula (I), $R^4$ is $CH_3$ or two $R^4$ groups are combined as —$CH_2$— to form a 5-membered ring.

In an embodiment of formula (I), each $R^3$ is independently a substituted or unsubstituted $C_1$-$C_6$ alkyl, or the $R^3$ groups are combined as —$CH_2$— or —$CH_2$—$CH_2$— to form a 5- or 6-membered ring.

In another embodiment of formula (I), $R^3$ is $CH_3$ or the $R^3$ groups are combined as —$CH_2$— to form a 5-membered ring.

In an embodiment of formula (I), $R^2$ is a substituted or unsubstituted $C_1$-$C_6$ alkyl.

In another embodiment of formula (I), $R^2$ is $CH_3$ or $CH_2CH_3$.

The compound of formula (I) may be administered as part of a pharmaceutical composition, wherein the pharmaceutical composition further comprises a pharmaceutically acceptable carrier or excipient.

Salts of the compounds described in the foregoing. Pharmaceutically acceptable salts, as used herein, refers to those salts of the compounds described herein that are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of the compounds described herein. These salts can be prepared in situ during the isolation and purification of the compounds or by separately reacting the purified compound in its free base form with a suitable organic or inorganic acid and isolating the salt thus formed.

Representative salts include the bromide, chloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, sulfoacetate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See Stahl and Wermuth, Pharmaceutical Salts: Properties, Selection, and Use, Wiley-VCH, 2008, which is incorporated herein by reference in its entirety, at least, for compositions taught therein.)

In an embodiment, the compound of formula (I), (II), (III), (IV), (V), or (VI) is a chloride (Cl$^-$) salt. In another embodiment, the compound of formula (I), (II), (III), (IV), (V), or (VI) is a salt of 2-sulfoacetate.

In another embodiment, the compound of formula (II), (III), (IV), or (V) is a salt of 2-sulfoacetate. In another embodiment, the compound of formula (VI) is a chloride salt.

As used herein, the terms alkyl, alkenyl, and alkynyl include straight- and branched-chain monovalent substituents. Examples include methyl, ethyl, isobutyl, 3-butynyl, and the like.

Heteroalkyl, heteroalkenyl, and heteroalkynyl are similarly defined but may contain O, S, or N heteroatoms or combinations thereof within the backbone.

The term cycloalkyl as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term heterocycloalkyl is a type of cycloalkyl group as defined above, and is included within the meaning of the term cycloalkyl, where at least one of the carbon atoms of the ring is replaced with a heteroatom such as, but not limited to, nitrogen, oxygen, sulfur, or phosphorus.

Aryl molecules include, for example, cyclic hydrocarbons that incorporate one or more planar sets of, typically, six carbon atoms that are connected by delocalized electrons numbering the same as if they consisted of alternating single and double covalent bonds. An example of an aryl molecule is benzene.

Heteroaryl molecules include substitutions along their main cyclic chain of atoms such as O, N, or S. When heteroatoms are introduced, a set of five atoms, e.g., four carbon and a heteroatom, can create an aromatic system. Examples of heteroaryl molecules include, furan, pyrrole, thiophene, imidazole, oxazole, pyridine, and pyrazine. Aryl and heteroaryl molecules can also include additional fused rings, for example, benzofuran, indole, benzothiophene, naphthalene, anthracene, and quinoline.

The alkyl, alkenyl, alkynyl, cycloalkyl, aryl, heteroalkyl, heteroalkenyl, heteroalkynyl, heterocycloalkyl, and heteroaryl molecules used herein can be substituted or unsubstituted.

As used herein, the term substituted includes the addition of an alkyl, alkenyl, alkynyl, cycloalkyl, aryl, heteroalkyl, heteroalkenyl, heteroalkynyl, heterocycloalkyl, or heteroaryl group (as described herein) to a position attached to the main chain of the alkyl, alkenyl, alkynyl, cycloalkyl, aryl, heteroalkyl, heteroalkenyl, heteroalkynyl, heterocycloalkyl, or heteroaryl, e.g., the replacement of a hydrogen by one of these molecules.

Examples of substitution groups include, but are not limited to, amino, amido, hydroxyl, halogen (e.g., F, Br, Cl, or I), cyano, nitro, haloalkyl, and carboxyl groups. Conversely, as used herein, the term unsubstituted indicates the alkyl, alkenyl, alkynyl, cycloalkyl, aryl, heteroalkyl, heteroalkenyl, heteroalkynyl, heterocycloalkyl, or heteroaryl has a full complement of hydrogens, i.e., commensurate with its saturation level, with no substitutions, e.g., linear decane (—$(CH_2)_9$—$CH_3$).

The compounds described herein may contain chiral centers. Such chiral centers may be of either the (R) or (S) configuration, or may be a mixture thereof. Thus, the compounds provided herein may be enantiomerically pure, or be stereoisomeric or diastereomeric mixtures. The separation of mixtures of optical isomers to obtain pure enantiomers is known in the art and is contemplated. Enantiomeric resolution may, for example, be achieved by fractional crystallization of salts with chiral acids or by chromatographic separation on chiral columns.

In the case of amino acid residues, such residues may be of either the L- or D-form. As used herein, the term amino acid refers to α-amino acids which are racemic, or of either the D- or L-configuration. The designation "L" preceding an amino acid refers to the L-isomer of the amino acid. The designation "DL" preceding an amino acid designation refers to a mixture of the L- and D-isomers of the amino acid. The chiral centers of the compounds provided herein may undergo epimerization in vivo. As such, the administration of a compound in its (L) form is equivalent, for compounds that undergo epimerization in vivo, to administration of the compound in its (D) form.

Synthesis and Characterization of Compounds

The compounds described herein can be prepared in a variety of ways. The compounds can be synthesized using synthetic methods known in the art of synthetic organic chemistry or variations thereon as appreciated by those skilled in the art. The compounds described herein can be prepared from readily available starting materials. Optimum reaction conditions may vary with the particular reactants or solvent used, but such conditions can be determined by one skilled in the art by routine optimization procedures.

Variations on compounds of formula (I), (II), (III), (IV), (V), and (VI) include the addition, subtraction, or movement of the various constituents as described for each compound. Similarly, as described above, when one or more chiral centers is present in a molecule the chirality of the molecule can be changed. Additionally, compound synthesis can involve the protection and deprotection of various chemical groups. The use of protection and deprotection, and the selection of appropriate protecting groups can be determined by one skilled in the art. The chemistry of protecting groups can be found, for example, in Wuts and Greene, Protective Groups in Organic Synthesis, 4$^{th}$ Ed., Wiley & Sons, 2006, which is incorporated herein by reference in its entirety. The synthesis and subsequent testing of various compounds as described by formulas (I), (II), (III), (IV), (V), and (VI) to determine efficacy is also contemplated.

Reactions to produce the compounds described herein can be carried out in solvents which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

Compositions

The compounds described herein or pharmaceutically acceptable salts or prodrugs thereof can be provided in a pharmaceutical composition. Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include an effective amount of the compounds described herein or a pharmaceutically acceptable salt or prodrug thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected substrate without causing significant undesirable biological effects or interacting in a deleterious manner with any of the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005. Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.).

Compositions containing the compounds described herein or pharmaceutically acceptable salts or prodrugs thereof suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and the like. Prolonged absorption of the injectable pharmaceutical form can be brought about by the use of agents delaying absorption, for example, aluminum monostearate and gelatin.

Solid dosage forms for oral administration of the compounds described herein or a pharmaceutically acceptable salt or prodrug thereof include capsules, tablets, pills, powders, and granules. In such solid dosage forms, the compounds described herein or a pharmaceutically acceptable salt or prodrug thereof is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration of the compounds described herein or pharmaceutically acceptable salts or prodrugs thereof include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include adjuvants, such as wetting, emulsifying, suspending, sweetening, flavoring, or perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions of the compounds described herein or pharmaceutically acceptable salts or prodrugs thereof for rectal administrations are preferably suppositories which can be prepared by mixing the compounds with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of the compounds described herein or pharmaceutically acceptable salts or prodrugs thereof include ointments, powders, sprays, and inhalants. The compounds described herein or pharmaceutically acceptable salts or prodrugs thereof are admixed under sterile conditions with a physiologically acceptable carrier and any preservatives, buffers, or propellants as may be required. Ophthalmic formulations, ointments, powders, and solutions are also contemplated as being within the scope of the compositions.

The compounds and compositions described above are useful in treating fungal or yeast infections in humans, e.g., including pediatric and geriatric populations, and animals, e.g., veterinary applications. Methods of using the compounds and compositions described herein comprise administering to a subject a therapeutically effective amount of the compounds or compositions described herein or a pharmaceutically acceptable salt or prodrug thereof.

Examples of yeast and fungal infections treatable by the methods described herein include fluconazole-resistant infections and infections caused by the genus *Candida* (e.g., candidiasis, including vaginal candidiasis and hospital acquired candidiasis), and fluconazole-resistant infections and infections caused by the genus *Aspergillus fumigatus*. The methods described herein are useful in treating infections caused by several species of *Candida*, including *Candida albicans, Candida guilliermondii, Candida glabrata, Candidia parapsilois, Candidia apicola, Candida tropicalis, Candida neoformans, Candid lustaniae*, and *Candida krusei*.

Further, the methods of treating fungal or yeast infections as described herein are useful in treating immunocompromised subjects. Immunocompromised subjects include, for example, HIV-positive subjects; subjects undergoing immunotherapy; cancer patients; individuals with viral infections; individuals with an autoimmune disease; patients with malignancies, leukemias, collagen-vascular diseases, or congenital or acquired immunodeficiency; organ-transplant recipients receiving immunosuppressive therapy; and other patients receiving immunosuppressive therapy. As used herein the term treating or treatment includes prevention; delay in onset; diminution, eradication, or delay in exacerbation of signs or symptoms after onset; and prevention of relapse.

The methods and compounds or compositions as described herein are useful for both prophylactic and therapeutic treatment of fungal or yeast infections. For prophylactic use, a therapeutically effective amount of the compounds or compositions described herein are administered to a subject prior to exposure (e.g., before or when traveling to a location where yeast or fungal infections are possible), during a period of potential exposure to yeast or fungal infections, or after a period of potential exposure to yeast or fungal infections.

Prophylactic administration can occur for several days to weeks prior to potential exposure, during a period of potential exposure, and for a period of time, e.g., several days to weeks, after potential exposure.

Therapeutic treatment involves administering to a subject a therapeutically effective amount of the compounds or compositions described herein after a yeast or fungal infection is diagnosed.

Administration of compounds or compositions described herein, or pharmaceutically acceptable salts or prodrugs thereof, can be carried out using therapeutically effective amounts of the compounds or compositions described herein or pharmaceutically acceptable salts or prodrugs thereof for periods of time effective to treat yeast or fungal infections.

The effective amount of the compounds or compositions described herein, or pharmaceutically acceptable salts or prodrugs thereof, may be determined by one of ordinary skill in the art, and includes exemplary dosage amounts for a mammal of from about 0.05 to about 100 mg/kg of body weight of active compound per day, which may be administered in a single dose or in the form of individual divided doses, such as from 1 to 4 times per day. Alternatively, the dosage amount can be from about 0.05 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about 5 mg/kg of body weight of active compound per day. Those of skill in the art will understand that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

In these methods, yeast or fungal infection, for example, can be further treated with one or more additional agents. For example, the methods of treating and preventing yeast or fungal infections as described herein can further include administering a second compound or composition to the subject. The second compound or composition used in the treatment of fungal or yeast infections can include antifungal compounds, antiviral compounds, or mixtures thereof. Examples of second compounds include triazole antifungals, thiazole antifungals, imidazole antifungals, polyene antifungals, echinocandin antifungals, allylamine antifungals, and amphotericin B. Combination treatments of the invention may exhibit synergy between the two agents.

In an embodiment, a compound of formula (I), (II), (III), (IV), (V), or (VI) is administered in combination with a triazole antifungal, thiazole antifungal, imidazole antifungal, polyene antifungal, echinocandin antifungal, allylamine antifungal, or amphotericin B. In an embodiment, the antifungal is a triazole antifungal. In a specific embodiment, the triazole antifungal is fluconazole.

In an embodiment, a compound of formula (II) is administered in combination with fluconazole. The combination of formula (II) and fluconazole may exhibit synergy when used in combination.

Antiviral compounds that can be used in combination with the compounds described herein include, for example, nucleoside polymerase inhibitors, non-nucleoside polymerase inhibitors, protease inhibitors, nucleoside or nucleotide reverse transcriptase inhibitors, non-nucleoside reverse transcriptase inhibitors, entry inhibitors, assembly inhibitors, integrase inhibitors, kinase inhibitors, enzyme inhibitors, maturation inhibitors, M2 inhibitors, and neuraminidase inhibitors. Examples of such additional antiviral compounds include, but are not limited to amantadine, rimantadine, oseltamivir (Tamiflu®, Roche Laboratories, Nutley, N.J.), zanamivir (Relenza®, GlaxoSmithKline, Philadelphia, Pa.), peramivir, raltegravir, Maraviros, enfuvititide, bevirimat, Vivecon™ (Myriad Genetics, Salt Lake City, Utah), Combivir® (zidovudine+lamivudine, AZT+3TC) (GlaxoSmithKline, Philadelphia, Pa.), Emtriva® (emtricitabine, FTC) (Gilead Sciences, Foster City, Calif.), Epivir® (lamivudine, 3TC) (GlaxoSmithKline, Philadelphia, Pa.), Epzicom® (Kivexa, abacavir+lamivudine, ABC+3TC) (GlaxoSmithKline, Philadelphia, Pa.), Retrovir® (zidovudine, AZT, ZDV) (GlaxoSmithKline, Philadelphia, Pa.), Trizivir® (abacavir+zidovudine+lamivudine, ABC+AZT+3TC) (GlaxoSmithKline, Philadelphia, Pa.), Truvada® (tenofovir DF+emtricitabine, TDF+FTC) (Gilead Sciences, Foster City, Calif.), Videx® & Videx EC® (didanosine, ddI) (Bristol-Myers Squibb, Princeton, N.J.), Viread® (tenofovir disoproxil fumarate, TDF) (Gilead Sciences, Foster City, Calif.), Zerit® (stavudine, d4T) (Bristol-Myers Squibb, Princeton, N.J.), Ziagen® (abacavir, ABC) (GlaxoSmithKline, Philadelphia, Pa.), Racivir™ (RCV) (Pharmasset, Princeton, N.J.), Amdoxovir™ (AMDX, DAPD) (RFS Pharma, Tucker, Ga.), apricitabine (SPD754, AVX754), elvucitabine (ACH-126,443, Beta-L-Fd4C), Immunitin® (HE2000, alpha-epibromide) (Hollis-Eden Pharmaceuticals, San Diego, Calif.), Proleukin® (aldesleukin, Interleukin-2, IL-2) (Chiron Corporation, Emeryville, Calif.), Remune® (HIV-1 Immunogen, Salk vaccine) (Orchestra Therapeutics, Carlsbad, Calif.), BAY 50-4798, IR103, Intelence™ (etravirine, TMC-125) (Tibotec Therapeutics, Irvine, Calif.), Rescriptor® (delavirdine, DLV) (Pfizer, New York, N.Y.), Sustiva® (Stocrin, efavirenz, EFV) (Bristol-Myers Squibb, Princeton, N.J.), Viramune® (nevirapine, NVP) (Boehringer Ingelheim, Ridgefield, Conn.), rilpivirine (TMC-278), Agenerase® (amprenavir, APV) (GlaxoSmithKline, Philadelphia, Pa.), Aptivus® (tipranavir, TPV) (Boehringer Ingelheim, Ridgefield, Conn.), Crixivan® (indinavir, IDV) (Merck, Whitehouse Station, N.J.), Invirase® (saquinavir, SQV) (Roche Laboratories, Nutley, N.J.), Kaletra® (Aluvia®, lopinavir/ritonavir, LPV/r) (Abbott Laboratories, Abbott Park, Ill.), Lexiva® (Telzir®, fosamprenavir, FPV) (GlaxoSmithKline, Philadelphia, Pa.), Norvir® (ritonavir, RTV) (Abbott Laboratories, Abbott Park, Ill.), Prezista® (darunavir, DRV) (Tibotec Therapeutics, Irvine, Calif.), Reyataz® (atazanavir, ATV) (Bristol-Myers Squibb, Princeton, N.J.), Viracept® (nelfinavir, NFV) (Pfizer, Inc., New York, N.Y.), Fuzeon® (enfuvirtide, ENF, T-20) (Roche Laboratories, Inc., Nutley, N.J.), Selzentry® (Celsentri®, maraviroc, UK-427,857) (Pfizer, Inc., New York, N.Y.), Victiviroc® (SCH-417690, SCH-D) (Schering-Plough, Kenilworth, N.J.), PRO 140 (Progenics Pharmaceuticals, Tarrytown, N.Y.), TNX-355 (Tanox, Inc., Houston, Tex.), Isentress® (raltegravir, MK-0518) (Merck, Whitehouse Station, N.J.), Elvitegravir™ (GS-9137) (Gilead Sciences, Foster City, Calif.), Bevirimat™ (PA-457) (Panacos Pharmaceuticals, Inc., Watertown, Mass.), and Droxia® or Hydrea® (hydroxyurea, HU) (Bristol-Myers Squibb, Princeton, N.J.).

For combination treatments, a compound of formula (I), (II), (III), (IV), (V), or (VI) may be administered simultaneously or sequentially with a second compound. For simultaneous administration or co-administration, the compound of formula (I), (II), (III), (IV), (V), or (VI) may be part of the same pharmaceutical composition with the second agent or the two agents may be administered as separate compositions.

The one or more additional agents and the compounds or compositions described herein, or a pharmaceutically acceptable salt or prodrug thereof, can be administered in any order, including simultaneous administration, as well as temporally spaced order of up to several days apart. The methods may also include more than a single administration of the one or more additional agents and/or the compounds or compositions described herein or a pharmaceutically acceptable salt or prodrug thereof. The administration of the one or more additional agent and the compounds or compositions described herein or a pharmaceutically acceptable salt or prodrug thereof may be by the same or different routes and concurrently or sequentially.

The examples below are intended to further illustrate certain aspects of the methods, compounds, and compositions described herein, and are not intended to limit the scope of the claims.

EXAMPLES

Example 1

Anti-Fungal/Anti-Yeast Activity

The anti-fungal or anti-yeast activity of compounds of formula (II), (III), (IV), (V), and (VI) were tested against *Candida* species, including *Candida albicans, Candida tropicalis, Candida, guilliermondii, Candida glabrata, Candida lusitaniae, Candida parapsilosis, Candida neoformans, Candida krusei*, and *Candida apicola*, as well as *Aspergillus fumigatus* was determined based upon the minimum inhibitory concentration (MIC) and minimum fungicidal concentrations (MFC) values as described below. An MFC/MIC ratio of less than four indicates that the compound is fungicidal; an MFC/MIC ratio of greater than four indicates that the compound is fungistatic. Fluconazole, an ergosterol inhibitor, and the beta-1,3-glucan inhibitor micafungin served as controls (See Tables 1 and 2).

MIC Determination—Broth Microdilution Method

The minimum inhibitory concentrations resulting in 80% growth inhibition (MIC of multiple *Candida* species (*Candida albicans, Candida tropicalis, Candida, guilliermondii, Candida glabrata, Candida lusitaniae, Candida parapsilois, Candida neoformans, Candida krusei*, and *Candida apicola*) as well as *Aspergillus fumigatus* to a set of formula (II), (III), (IV), and (V) was determined in accordance with the guidelines in CLSI document M27-A2 (Clinical and Laboratory Standards Institute; Wayne, Pa.). The total volume of cells and drug was 100 µL per microtiter well, and each drug was diluted in RPMI to achieve final concentrations of 0.2-100 µg/ml. Uninoculated cultures were used as a reference standard. Stock inoculum suspensions were prepared from 24 hour cultures on YPD (yeast extract/peptone/dextrose) media at 30° C.

For MIC determinations, an inoculum of $1.0 \times 10^3$ cells of *Candida* and $2.0 \times 10^3$ cells of *Aspergillus* per well were used, and cells in diluted drugs were prepared in RPMI-1640 medium. MICs were determined both visually and spectrophotometrically at 24 hours and 48 h at 550 nm using a micro plate reader. The MIC$_{80}$ endpoint was measured as the lowest drug concentration resulting in a reduction of growth of 80% or more compared with growth of the control.

MFC Determination

Plating Method

The minimum fungicidal concentrations (MFCs) may be determined for each drug-isolate-medium combination as follows. After 48 hours of incubation, 100 μL of each drug-isolate-medium combination (2 plates) is subcultured onto YPD plates (100 μL of solution is spread over the YPD plate). The subcultured solutions are obtained from each well that showed complete inhibition (100% or an optically clear well) from the last positive well (growth similar to that for the growth control well) and from the growth control (drug-free medium). The plates are then incubated at 30° C. for 48 hours. The MFC is measured as the lowest drug concentration that shows either no growth or fewer than five colonies to obtain approximately 99% killing activity.

Example 2

Drop Plate Assay of Formula (II) (NSC 156627) with *C. albicans*

Growth inhibition was visualized by plating 5 μl of ten-fold serial dilutions of cells onto YPD agar plates containing compounds at indicated concentrations. Cells were grown overnight in YPD broth at 30° C., washed with saline, and standardized by hemacytometer counts. Growth was photographed and evaluated after 48 h of incubation at 30° C. The results of this drop plate assay are shown in FIG. 1.

Example 3

Toxicity Assays

Neutral Red Uptake Assay

The neutral red uptake assay is a cytotoxicity test that is based on the ability of viable cells to incorporate and bind the supra-vital dye neutral red in the lysosomes. This weakly cationic dye penetrates cell membranes by non-ionic passive diffusion and concentrates in the lysosomes, where it binds by electrostatic hydrophobic bonds to anionic and phosphate groups of the lysosomal matrix. The dye is then extracted from the viable cells using an acidified ethanol solution, and the absorbance of the solubilized dye is read. When the cell dies or the pH gradient is reduced, the dye is not retained and consequently, the amount of retained dye is proportional to the number of viable cells. Most primary cells and cell lines can be used for this method. The HepG2 and Huh7, two human hepatoma cell lines, are used for this study. The cells are seeded in 96-well tissue culture plates and treated for 48 hours with the compounds. The plates are then incubated for 2 hours with a medium containing neutral red. The cells are subsequently washed, the dye is extracted in each well, and the absorbance is read using a spectrophotometer.

MTT Assay

The MTT assay is a colorimetric assay that measures the reduction of yellow 3-(4,5-dimethythiazol-2-yl)-2,5-diphenyl tetrazolium bromide (MTT) by mitochondrial succinate dehydrogenase. The MIT enters the cells and passes into the mitochondria where it is reduced to an insoluble, dark purple, formazan product. The cells are then solubilized with an organic solvent (e.g., isopropanol) and the released, solubilized formazan reagent is measured spectrophotometrically. Since reduction of MTT can only occur in metabolically active cells, the level of activity is a measure of the viability of the cells.

Cells of the HepG2 liver cell, NIH/3T3 fibroblast cell, or 293T kidney cell were seeded in a 96 well plate. The plate was incubated overnight at 37° C. in a humidified incubator, 5% CO$_2$. Compounds of formula (II), (III), (IV), (V), and (VI) were added to the plate. Different concentrations of drug were tested in triplicate along with a negative control. The final volume was adjusted to 100 μl per well. The plate was incubated overnight at 37° C. in a humidified incubator, 5% CO$_2$. After 24 hours and 48 hours, MTT reagent (5 mg/ml, 10 μl/100 μl per well of the 96 well plate) was added and incubated at 37° C. for 3 hours. After 3 hours, 100 μl of the DMSO solution was added to each well and the plate was rocked at room temperature for 1 hour. The plate was then read on a plate reader at 550 nM. The results are shown below in tables 1 and 2.

Example 4

E-Test of Formula (II) and Fluconazole Against *C. albicans* (Wild Type)

Figure 2:
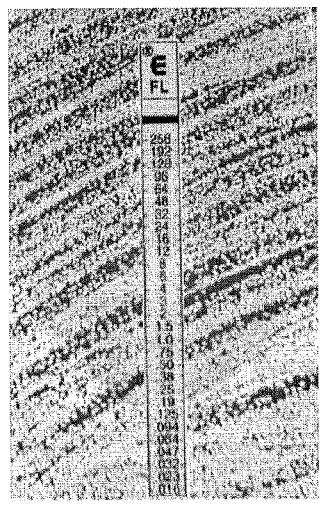
FIG. 2: E-test shows synergy of NSC156627 (formula II) and fluconazole against *C. albicans* wild type.
Figure 2:
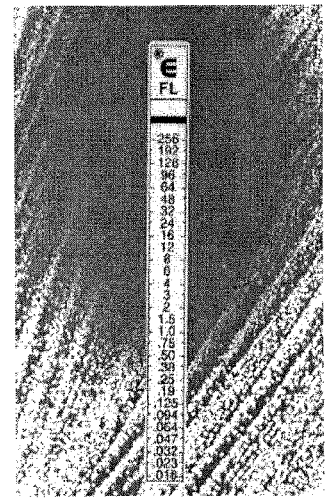

E test strips (Biomerieux) containing a graded series of fluconazole concentration are placed on a YPD plate that had been previously inoculated to confluency with *C. albicans*. The strip plate that was inoculated, is incubated for 48 h at 30° C. The zone of inhibition at the lowest concentration of fluconazole is read as the MIC. The results, shown in FIG. 2, indicate synergy between the compound of formula (II) and fluconazole.

The compounds and methods of the appended claims are not limited in scope by the specific compounds and methods described herein, which are intended as illustrations of a few aspects of the claims and any compounds and methods that are functionally equivalent are within the scope of this disclosure. Various modifications of the compounds and methods in addition to those shown and described herein are intended to fall within the scope of the appended claims. Further, while only certain representative compounds, methods, and aspects of these compounds and methods are specifically described, other compounds and methods are intended to fall within the scope of the appended claims. Thus a combination of steps, elements, components, or constituents may be explicitly mentioned herein; however, all other combinations of steps, elements, components, and constituents are included, even though not explicitly stated.

TABLE 1

Activity (MIC$_{80}$) and toxicity (MTT) for compounds of formula (II), (III), (IV), and (V):

| (μg/ml) | Fluconazole | Itraconazole | 156627 | 156624 | 157108 | 160459 |
|---|---|---|---|---|---|---|
| *C. albicans* (SC5314) | 0.25 | | 0.5 | 4 | 1 | 4 |
| *C. albicans* (CaMDR) | 32 | | 0.05 | 0.2 | 0.2 | 0.1 |
| *C. guilliermondii* | 2 | | 0.5 | 4 | 2 | 4 |

TABLE 1-continued

Activity (MIC$_{80}$) and toxicity (MTT) for compounds of formula (II), (III), (IV), and (V):

| (μg/ml) | Fluconazole | Itraconazole | 156627 | 156624 | 157108 | 160459 |
|---|---|---|---|---|---|---|
| C. glabrata | 2 | <0.2 | 1 | 0.2 | 0.5 | |
| C. tropicalis | 0.5 | | 0.5 | 4 | 2 | 4 |
| C. parapsilosis | 1 | | 1 | 8 | 2 | 8 |
| C. lnslianiae | 2 | | <0.2 | 1 | 0.2 | 1 |
| C. apicola | 0.25 | | 0.5 | 4 | 1 | 4 |
| C. krnsei | 32 | | 0.5 | 4 | 2 | 4 |
| C. neoformans H99 | 4 | | 1 | 8 | 2 | 8 |
| C. neoformans JEC-21 | 2 | | <0.2 | 1 | 0.2 | 0.5 |
| A. fumigatus H11-20 | | 0.5 | 0.5 | 4 | 1 | 4 |
| A. fumigatus AF293 | | 0.5 | 0.5 | 4 | 1 | 4 |
| MDR A. fumigatus | | >100 | 0.5 | 4 | 1 | 4 |
| HepG2 liver cell | NA | NA | 25 | 80 | 64 | 50 |
| NIH/3T3 Fibroblast cell | NA | NA | 40 | >100 | 100 | 80 |
| 293T kidney cell | NA | NA | 25 | 80 | 70 | 60 |

TABLE 2

Activity (MIC$_{80}$) and toxicity (MTT) for formula (VI):

| Species | 403831 MIC (μg/ml) |
|---|---|
| C. albicans (SC5314) | 1 |
| C. albicans (CaMDR) | 0.1 |
| C. guilliermondii | 1 |
| C. glabrata | 0.25 |
| C. tropicalis | 1 |
| C. parapsilosis | 2 |
| C. lusitaniae | 0.5 |
| C. apicola | 1 |
| C. krusei | 2 |
| C. neoformans (H99) | 0.5 |
| C. neoformans (JEC-21) | 0.5 |
| A. fumigatus (H11-20) | 1 |
| A. fumigatus (AF293) | 1 |
| MDR A. fumigatus | 1 |
| HepG2 liver cell | 80 |
| NIH/3T3 Fibroblast cell | 96 |
| 293T kidney cell | 80 |

The invention claimed is:

1. A method of treating a fungal or yeast infection in a subject comprising administering to the subject a therapeutically effective amount of a compound of formula (III):

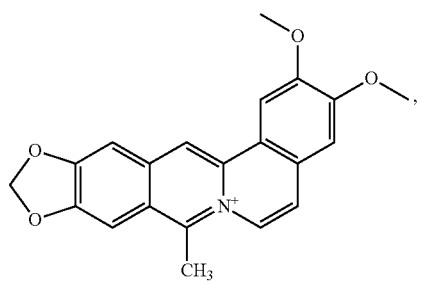

or formula (IV):

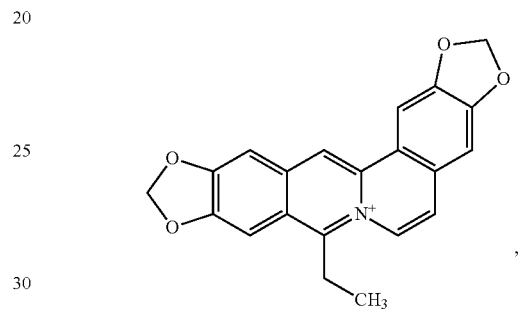

or a pharmaceutically acceptable salt thereof, to a subject in need thereof.

2. The method of claim 1; wherein the pharmaceutically acceptable salt is a bromide, chloride, sulfate, sulfoacetate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, or laurylsulphonate salt.

3. The method of claim 1; wherein the pharmaceutically acceptable salt is chloride or sulfoacetate.

4. The method of claim 1; wherein the subject is immunocompromised.

5. The method of claim 1; wherein the subject is being treated for a candidiasis and/or aspergillosis infection.

6. The method of claim 5; wherein the candidiasis infection is caused by one or more of the following strains:

*Candida albicans, Candida tropicalis, Candida guilliermondii, Candida glabrata, Candida lusitaniae, Candida parapsilosis, Candida neoformans, Candida krusei,* and/or *Candida apicola.*

7. The method of claim 5; wherein the aspergillosis infection is caused by *Aspergillus fumigates.*

8. The method of claim 1; wherein the subject is being treated for a drug resistant fungal infection.

9. The method of claim 1; further comprising the administration of a second antifungal compound.

10. A method of treating a fungal or yeast infection in a subject comprising administering to the subject a therapeutically effective amount of a compound of formula (II):

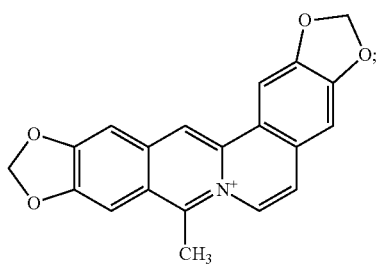 [SMILES: Cc1c2cc3c(cc2cc2c4cc5c(cc4cc[n+]12)OCO5)OCO3]

and
wherein the second antifungal compound is flucanazole.

11. A method of treating a fungal or yeast infection in a subject comprising administering to the subject a therapeutically effective amount of a pharmaceutical composition comprising one or more pharmaceutically acceptable excipient(s) and a compound of
formula (III):

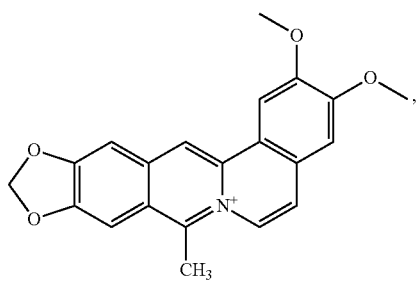 [SMILES: COc1cc2cc[n+]3c(C)c4cc5c(cc4cc3c2cc1OC)OCO5]

or formula (IV):

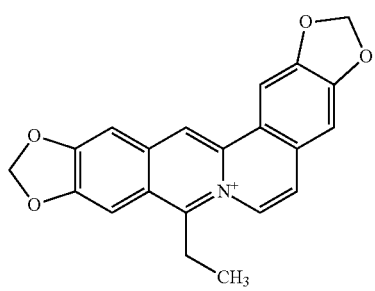 [SMILES: CCc1c2cc3c(cc2cc2c4cc5c(cc4cc[n+]12)OCO5)OCO3]

to a subject in need thereof.

12. The method of claim 11; where the compound of formula (I) is a bromide, chloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, or laurylsulphonate salt.

13. The method of claim 11; wherein the composition is administered systemically.

14. The method of claim 11; wherein the composition is administered locally to the infection.

15. The method of claim 14; wherein the composition further comprises a second anti-fungal agent.

* * * * *